United States Patent
Hobson

(10) Patent No.: US 10,215,310 B2
(45) Date of Patent: Feb. 26, 2019

(54) STACKABLE ROUTING CLIP

(71) Applicant: IMAGE INDUSTRIES INC., Huntley, IL (US)

(72) Inventor: Blake Hobson, Lakewood, IL (US)

(73) Assignee: IMAGE INDUSTRIES INC., Huntley, IL (US)

(*) Notice: Subject to any disclaimer, the term of this patent is extended or adjusted under 35 U.S.C. 154(b) by 336 days.

(21) Appl. No.: 15/044,943

(22) Filed: Feb. 16, 2016

(65) Prior Publication Data

US 2016/0169418 A1  Jun. 16, 2016

Related U.S. Application Data

(63) Continuation of application No. 13/422,685, filed on Mar. 16, 2012, now Pat. No. 9,296,059.

(60) Provisional application No. 61/545,216, filed on Oct. 10, 2011.

(51) Int. Cl.
| | |
|---|---|
| *F16L 3/26* | (2006.01) |
| *A61K 31/551* | (2006.01) |
| *A61K 45/06* | (2006.01) |

(52) U.S. Cl.
CPC .............. *F16L 3/26* (2013.01); *A61K 31/551* (2013.01); *A61K 45/06* (2013.01)

(58) Field of Classification Search
CPC .......... F16L 3/26; A61K 31/551; A61K 45/06
See application file for complete search history.

(56) References Cited

U.S. PATENT DOCUMENTS

| | | |
|---|---|---|
| 2,062,098 A | 11/1936 | Macchesney |
| 2,830,344 A | 4/1958 | Crosby |
| 2,871,536 A | 2/1959 | Childress |
| 3,051,424 A | 8/1962 | Duhamel |
| 3,120,938 A | 2/1964 | Lucas |
| 3,352,414 A | 11/1967 | Kuoni |
| 3,457,600 A | 7/1969 | Lennon |
| 3,553,794 A | 1/1971 | Kneidl et al. |
| 3,722,669 A | 3/1973 | Meier et al. |
| 3,750,239 A | 8/1973 | Styner |

(Continued)

FOREIGN PATENT DOCUMENTS

| | | |
|---|---|---|
| CA | 2665890 | 4/2010 |
| CN | 1271822 | 11/2000 |

(Continued)

OTHER PUBLICATIONS

Extended European Search Report, in International Application No. PCT/US2012/029457, dated Jul. 29, 2016, 7 pages.

(Continued)

*Primary Examiner* — Robert Sandy
*Assistant Examiner* — Louis A Mercado
(74) *Attorney, Agent, or Firm* — McAndrews, Held & Malloy, Ltd.

(57) ABSTRACT

A stackable routing clip for installation on machinery using a weld tool. The stackable routing clip has a body and at least one wing section. A weld projection extends from a lower face of the body. Each wing section may extend from the body and include a routing port that receives the insertion of a cable tie used to secure cables to the stackable routing clip. The stackable routing clip is configured so that a plurality of the stackable routing clips may be grouped together to form a stack. The clips may be stacked together in a dispenser that is used to dispense of individual clips when a clip is to be welded by the weld tool to the machinery. The weld tool may melt the weld projection and plunge the clip into the resultant molten metal for a quick and strong weld.

14 Claims, 6 Drawing Sheets

(56) References Cited

U.S. PATENT DOCUMENTS

| | | |
|---|---|---|
| 3,996,446 A | 12/1976 | Tauern et al. |
| 4,479,625 A | 10/1984 | Martz |
| 5,054,614 A | 8/1991 | Glaus et al. |
| 5,390,883 A | 2/1995 | Songhurst |
| 5,541,383 A | 7/1996 | Renner et al. |
| 5,560,526 A | 10/1996 | Jantzen et al. |
| 5,582,297 A | 12/1996 | Carter |
| 5,927,497 A | 7/1999 | Baumgartner et al. |
| 7,861,981 B2 | 1/2011 | Olver |
| 2001/0019093 A1 | 9/2001 | Koziol |
| 2008/0078891 A1 | 4/2008 | Hobson |
| 2010/0096511 A1 | 4/2010 | Olver |

FOREIGN PATENT DOCUMENTS

| | | |
|---|---|---|
| CN | 1520498 | 8/2004 |
| CN | 1260605 | 7/2007 |
| CN | 201487393 | 5/2010 |
| JP | S55130384 A | 10/1980 |
| JP | 2002233037 A | 8/2002 |

OTHER PUBLICATIONS

First Office Action and Search Report, Chinese Application No. 2012800141884, dated Mar. 31, 2015, 8 pages.

Second Office Action, Chinese Application No. 2012800141884, dated Oct. 16, 2015, 19 pages.

PCT, International Preliminary Report on Patentability, in International Application No. PCT/US2012/029457, dated Oct. 3, 2013, 7 pages.

PCT, International Searching Authority, Notification of Transmittal of the International Search Report and the Written Opinion of the International Search Authority, or the Declaration (dated Jul. 13, 2012) International Application No. PCT/US2012/29457, filed Mar. 16, 2012, Applicant—Image Industries.

STACKABLE ROUTING CLIP

RELATED APPLICATIONS

This application is a continuation of U.S. patent application Ser. No. 13/422,685, entitled "Stackable Routing Clip," filed on Mar. 16, 2012, now U.S. Pat. No. 9,296,059, which makes reference to, claims priority to, and claims benefit from U.S. Provisional Patent Application Ser. No. 61/454,216, entitled "Stackable Routing Clip," filed on Mar. 18, 2011. The entire contents of each above-mentioned prior-filed application is hereby expressly incorporated herein by reference.

BACKGROUND OF THE INVENTION

Embodiments of the present invention relate to stackable routing clips. More specifically, embodiments of the present invention relate to routing clips that may be stacked in a dispenser, such as a magazine for a weld tool, and be individually dispensed so as to be position at, and welded to, a target location on machinery.

Various types of machinery employee mounts that are used to route and/or secure wires, cables, tubes, flexible pipe, hoses, and the like (collectively cables) in or around the machinery, including, for example, construction equipment and service vehicles. In use, the cables may be secured to one or more mounts that are affixed to one or more pieces or components of the machinery. Such mounts generally secure the cables at a desired location and/or in a relatively close proximity to the machinery. Further, such mounts may be used for a number of different purposes, including, for example, preventing the cables from moving or being moved to locations that may interfere with the operation of machinery, and/or to protect the cables and attached components from being entangled and/or pulled on by other machinery or people.

One type of mount used for construction equipment is an oval shaped or open-ended mount that is formed from thick pieces of wire, such as, for example, 3/16" diameter wire. Such wires are often carried by workers, such as in bags, that are manipulated into position prior to being mounted to the machinery. When being mounted to machinery, the worker typically needs to use at least one hand to hold the oval-shaped or open-ended mount at a desired location on the machinery. While holding the mount at or around the desired location with one hand, the worker uses his/her other hand to weld the mount to the machinery. For example, while holding the mount in position with a first hand, the user may use the second hand to operate a welding torch to weld the mount to the machinery. Further such mounts may require two or more welds, such as a weld to secure the oval or open-ended shape of the manipulated wire and a weld to secure the mount to the machinery.

However, the procedure of requiring the worker to retrieve the relatively straight wire to be used as the mount, hold the mount with the worker's first hand at or around a desired location on the machinery, and apply one or more welds to the hand-held mount with the worker's second hand to secure the mount to the machinery presents a number of issues. For example, such mounts are often relatively small in size. Therefore, the worker's first hand that is holding the mount is typically in relative close proximity to the welding site. Such close proximity to the welding site causes the potential for burn injuries to the worker, such as burns caused by the heat or sparks generated during welding. Additionally, the close proximity of at least the worker's first hand to the welding site may put the worker at risk of being injured through inadvertent contact with the welding gun, wire, or stick. Further, using both hands while securing the mount to the machinery may cause the worker's head to be relatively close to the welding site, which may heighten the worker's possible exposure to harmful gases and fumes that are produced during welding. Additionally, the above process, or variations thereof, may be relatively time consuming, and thus increase production costs.

BRIEF SUMMARY OF THE INVENTION

An aspect of the present invention is a stackable routing clip that has a body and at least one wing section. The body includes an upper face and a lower face. The body also includes a weld projection that extends from the lower face of the body. Additionally, the at least one wing section has a top surface, a bottom surface, and a routing port. The routing port is configured to receive the insertion of at least one cable tie.

Another aspect of the present invention is a stackable routing clip to be secured to machinery by a weld tool. The stackable routing clip includes a body that has an upper face, a lower face, and a weld projection. The weld projection extends from the lower face of the body. Additionally, the body further includes a first wing section and a second wing section. The first and second wing sections each have a top surface, a bottom surface, and a routing port. Further, the top surface of the first and second wing sections extends away from the upper face of the body. The routing port is configured to receive the insertion of a cable tie. Additionally, the body and first and second wings are configured to allow a plurality of the stackable routing clips to be stacked together in a dispenser for a weld tool.

Another aspect of the present invention is a stackable routing clip that is to be secured to machinery by a weld tool. The stackable routing clip has a unitary construction that includes a body and at least one wing section. The body has an upper face, a lower face, a first side, a second side, a weld projection, and a groove. The weld projection extends from the lower face of the body. The groove is disposed at an opposing position to the weld projection along the upper face. Additionally, the at least one wing section has a top surface, a bottom surface, and a routing port. Further, the at least one wing section extends away from the body. The body and the at least one wing are also configured to allow a plurality of the stackable routing clips to be stacked together.

Figure 1:
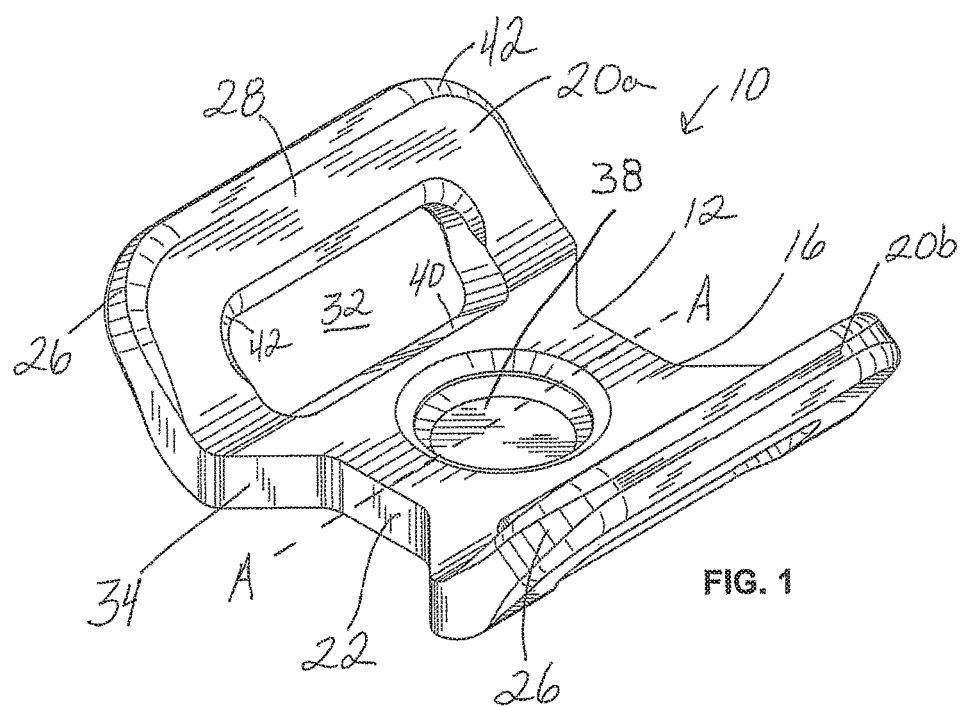
FIG. 1 is a front side perspective view of a stackable routing clip according to an embodiment of the present invention.
Figure 2:
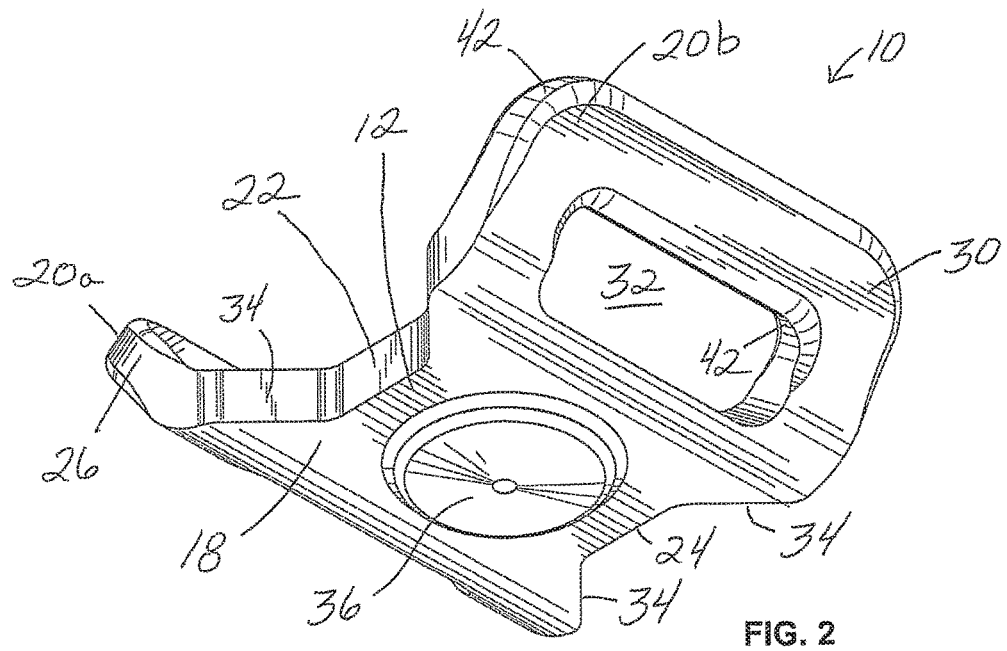
FIG. 2 is a bottom side perspective view of a stackable routing clip according to an embodiment of the present invention.
Figure 3:
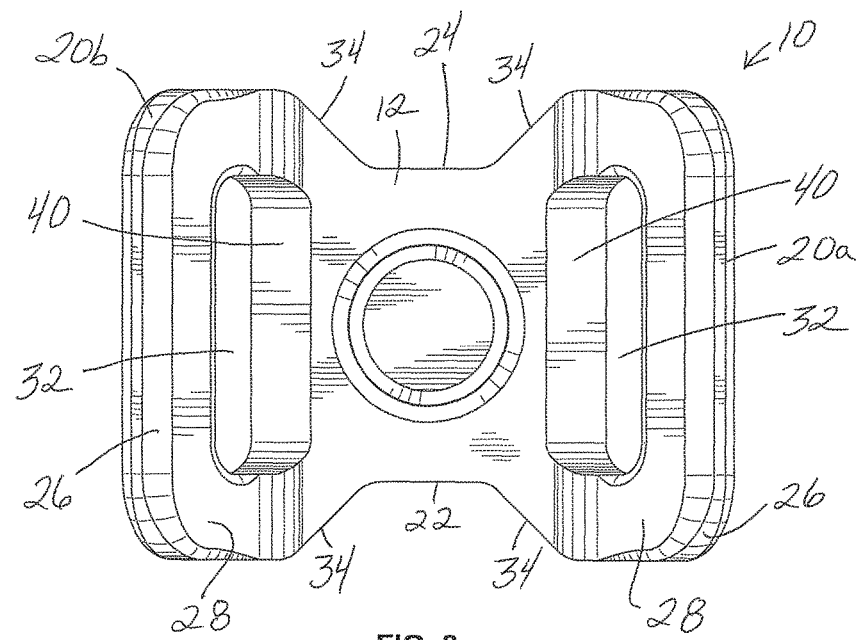
FIG. 3 is a top view of a stackable routing clip according to an embodiment of the present invention.
Figure 4:
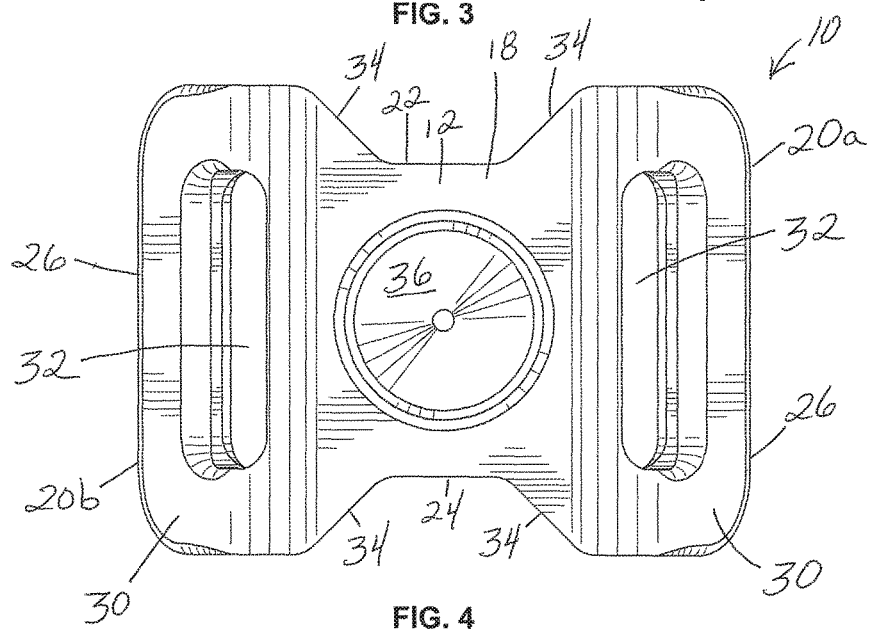
FIG. 4 is a bottom view of a stackable routing clip according to an embodiment of the present invention.
Figure 5:
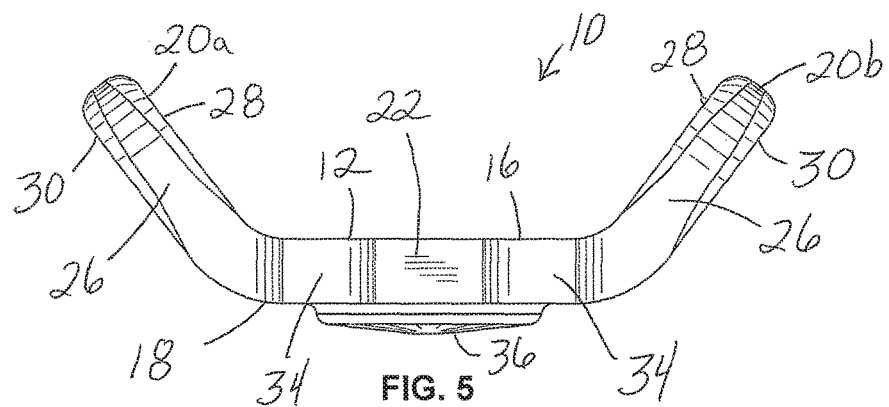
FIG. 5 is a front side view of a stackable routing clip according to an embodiment of the present invention.
Figure 6:
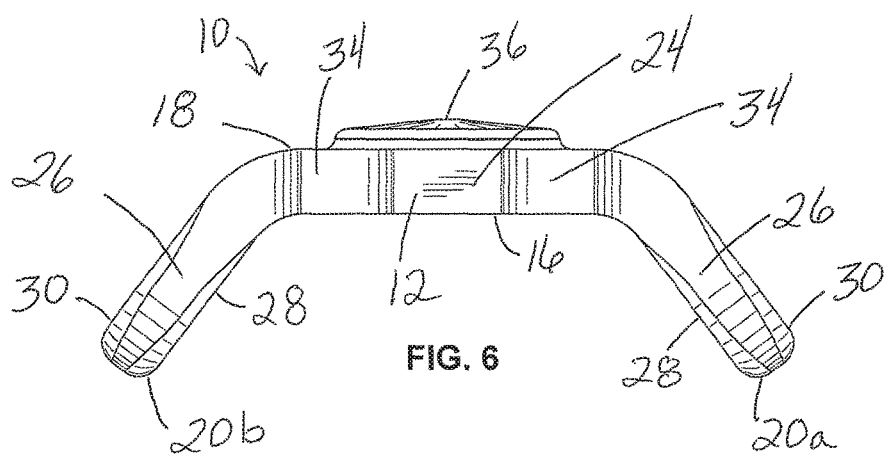
FIG. 6 is a rear side view of an inverted stackable routing clip according to an embodiment of the present invention.
Figure 7:
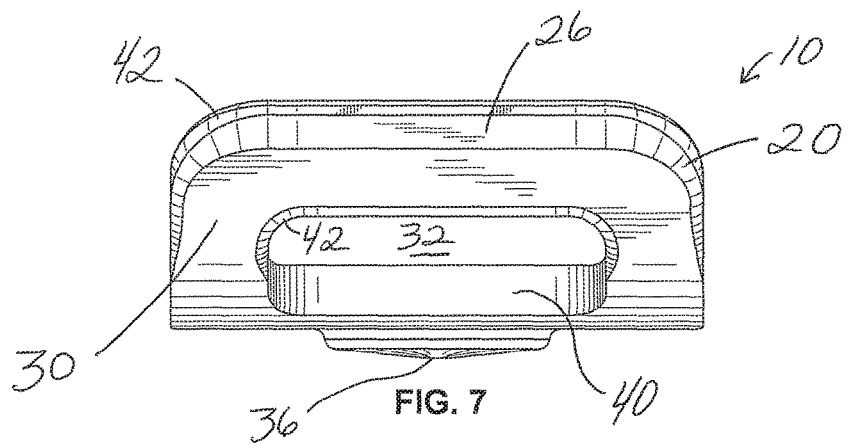
FIG. 7 is a left or right side view of a stackable routing clip according to an embodiment of the present invention.

The foregoing summary, as well as the following detailed description of certain embodiments of the present invention, will be better understood when read in conjunction with the appended drawings. For the purpose of illustrating the invention, there is shown in the drawings, certain embodiments. It should be understood, however, that the present invention is not limited to the arrangements and instrumentalities shown in the attached drawings.

DETAILED DESCRIPTION OF THE INVENTION

FIGS. 1 to 7 illustrate a stackable routing clip 10 according to an embodiment of the present invention. While FIGS. 1 to 7 illustrate a stackable routing clip 10 having a particular appearance, the stackable routing clip 10 is susceptible to having a variety of other, different appearances. According to certain embodiments, the stackable routing clip 10 may have a unitary construction that is made from a variety of different weldable materials, including, for example, carbon steel, stainless steel, and aluminum, among others. As shown in at least FIGS. 1 to 4, the stackable routing clip 10 includes a body 12 that has upper and lower faces 16, 18 that are positioned on generally opposite sides of the body 12. The body 12 may have a variety of different configurations, such as, for example, being generally rectangular, square, triangular, trapezoidal, circular, oval, and non-circular, among other configurations. In the illustrated embodiment, the body 12 is configured to include first and second sides 22, 24. Further, the general geometrical configuration of the body 12 may also include various contours that are configured to reduce the material size, cost, and/or weight of the stackable routing clip 10 or to improve the dispensing or handling of the stackable routing clip 10, among other reasons. Additionally, although the body 12 and the stackable routing clip 10 is shown in the illustrated embodiment to be generally symmetrical about centerline A-A in FIG. 1, the stackable routing clip 10 may also have asymmetrical configurations.

The stackable routing clip 10 further includes at least one wing section 20 that extends away from the body 12. According to the illustrated embodiment, the body 12 includes a first wing section 20a and a second wing section 20b that extend from generally opposite ends of the body 12. However, according to other embodiments, only one wing section 20 may extend from the body 12, or the wing sections 20a, 20b may also extend from the first side 22 and/or the second side 24 of the body 12. The number of wing sections 20 that extend from the body 12 may be depend on a variety of different considerations, including, for example, the size of the wing section 20, the size and/or shape of the body 12, and the number of cables to be routed through, around, or between the stackable routing clip(s) 10, among other considerations.

According to the illustrated embodiment, the first and second wing sections 20a, 20b have the generally same shape and/or configuration. For example, referencing FIGS. 1, 2, 5, and 6, in the illustrated embodiment, each wing section 20a, 20b extends from the body 12 to form an obtuse angle, such as, for example 127-degree angle that may be formed between an upper face of the body 12 and a top surface 28 of a wing section 20a. However, according to other embodiments, one or more of the wing sections 20a may form an angle with the body 12 that is different than the angle formed by the extension of another wing section 20b. Further, according to certain embodiments, the size and/or shape of at least one wing section 20a may be different than that of another wing section 20b.

In the illustrated embodiment, the wing section 20a, 20b includes an outer side 26, the top surface 28, a bottom surface 30, and a routing port 32. The routing port 32 is configured to receive the insertion of one or more cable ties that are used to secure cable(s) that is/are being routed through, around, and/or between the stackable routing clip(s) 10. The routing ports 32 may also include angled surfaces or ramps 40 that facilitate the routing of the cable tie into and/or through the routing ports 32. Additionally, corner surfaces of the stackable routing clip 10 may be chamfered or otherwise include radii 42 that may assist in preventing or minimizing damage and/or premature cable failure associated with friction between the stackable routing clip 10 and cables that are secured to the stackable clips 10.

The outer side 26 of the wing section 20a may extend around at least portion of the wing section 20a, 20b. Further, in the illustrated embodiment in which the stackable routing clip 10 has two wing sections 20a, 20b, the outer side 26 for each wing section 20a, 20b extends from the first side 22 to second side 24 of the body 12, or vice versa. Further, the first and second sides 22, 24 or the outer side 26 may include contours, such as one or more extensions 34, which join the first and second sides 22, 24 to the outer side 26.

The body 12 also includes a weld projection 36, which extends away from the lower face 18 of the body 12. The weld projection 36 may be formed in the body 12, such as, for example, by stamping the body 12, machining of the stackable routing clip 10, or by a mold or die used to form the stackable routing clip 10. Thus, according to certain embodiments, the formation of the weld projection 36 may create a corresponding indentation or groove 38 that is positioned in the upper face 16 of the body 12. The groove 38 may be configured to receive the placement of a portion of a weld tool when the stackable routing clip 10 is being secured at target location on a piece of machinery.

Additionally, according to certain embodiments, the weld projection 36 may include flux that may assist in the welding operation. The flux may be used to remove and/or to prevent the oxidation from the materials that are being welded together. According to certain embodiments, the flux may be applied, such as, for example, coated, onto at least a portion of an exterior surface of the weld projection 36. However, according to other embodiments, the flux may be contained in an inner portion of the weld projection 36. For example, the weld projection 36 may include a orifice that is configured to house flux that is to be used when the stackable mounting clip 10 is being secured to the machinery.

Figure 8:
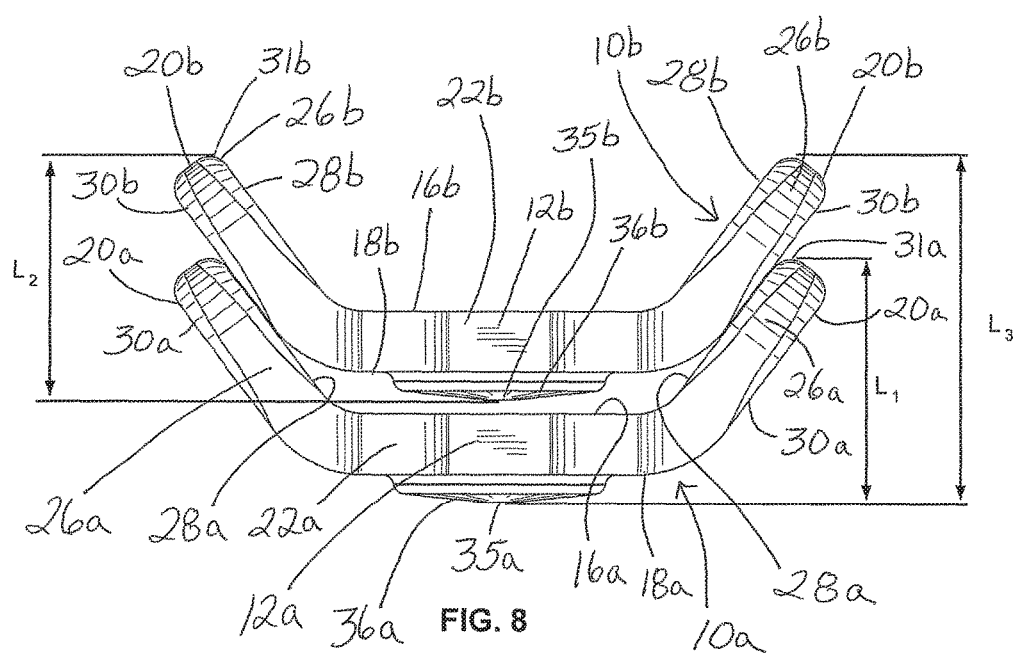
FIG. 8 is a front side view of two stackable routing clips stacked together according to an embodiment of the present invention.

FIG. 8 is a front side view of two stackable routing clips 10a, 10b that have been stacked together according to an embodiment of the present invention. In the illustrated embodiment, the stackable routing clips 10a, 10b are configured such that the bottom surface 30b of the second stackable routing clip 10b engages the top surface 28a of the first stackable routing clip 10a. As shown, the first stackable routing clip 10a has a length ($l_1$) in generally the "L" direction (as shown in FIG. 8) that extends from approximately a base 35a of the weld projection 36a to an upper portion 31a of a wing section 20a. Similarly, the second stackable routing clip 20b has a length ($l_2$) that extends from approximately a base 35b of the weld projection 36b to an upper portion 31b of a wing section 20b. As illustrated, when stacked, the stackable routing clips 10a, 10b have a stacked length ($l_3$) that extends from the base 35a of the weld projection 36a of the first stackable routing clip 10a to the upper portion 31b of the wing section 20b of the second stackable routing clip 10b. As shown, this stacked length ($l_3$) of the stacked clips 10a, 10b is less than the sum of the individual lengths ($l_1$, $l_2$) of the first and second stackable clips 10a, 10b. More specifically, according to the illustrated embodiment, $l_3 < l_1 + l_2$.

In the illustrated embodiment, the weld projection 36 of the second stackable routing clip 10b is shown to be elevated from the body 12a of the first stackable clip 10a. However, the stackable routing clips 10a, 10b may have a variety of different stacking configurations. For example, the angle between the body 12a, 12b and the associated wing sections 20 may be increased such that at least a portion of the weld projection 36b on the second stackable routing clip 10b may be positioned in the groove 38 of the adjacent first stackable routing clip 10a, thereby allowing individual clips 10 from a stack of stackable routing clips 10 to be dispensed in a transverse manner. According to such an embodiment, the angle between the body 12a, 12b and the wing sections 20 may be such that the lower face 18b of the body 12b of the second stackable routing clip 10b may engage the upper face 16a of the body 12a of the stackable routing clip 10a.

Figure 9:
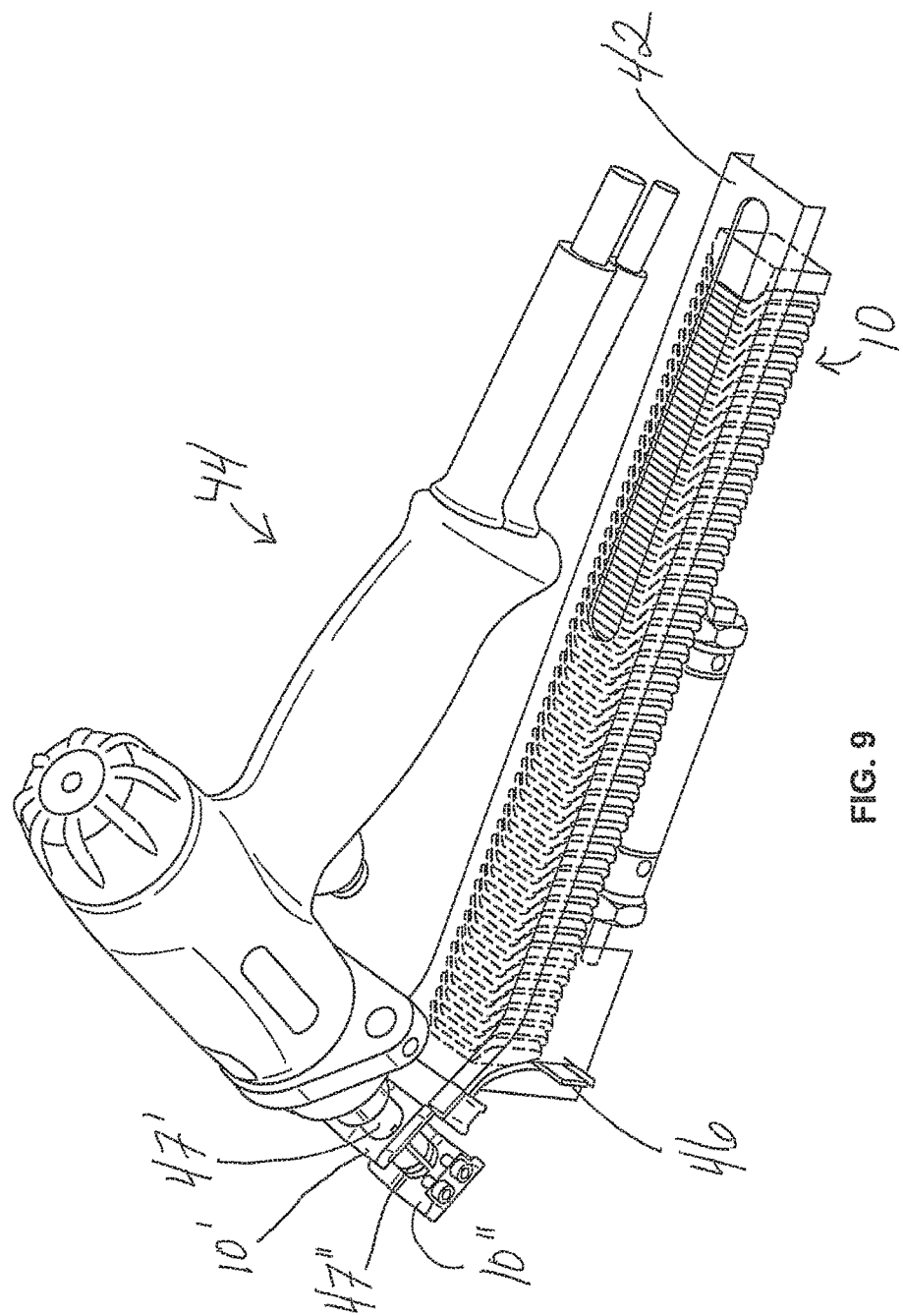
FIG. 9 is a perspective view of a first weld tool fitted with a magazine holding a plurality of stackable routing clips.

FIG. 9 illustrates a plurality of stackable routing clips 10 stacked together in a dispenser, such as, for example, a magazine 42, which is operably attached to a weld tool 44. According to certain embodiments, the weld tool 44 is of similar design to the stud welding tools manufactured and sold by Image Industries, Inc., of Huntley, Ill. The magazine 42 is configured to hold a plurality of stackable routing clips 10. For example, according to certain embodiments, the magazine 42 may be configured to hold at least 50 stackable routing clips 10. While FIG. 9 illustrates a hand held weld tool 44, the stackable clips 10 may also be dispensed for a dispenser that is operably attached to a robotic welder.

Figure 10:
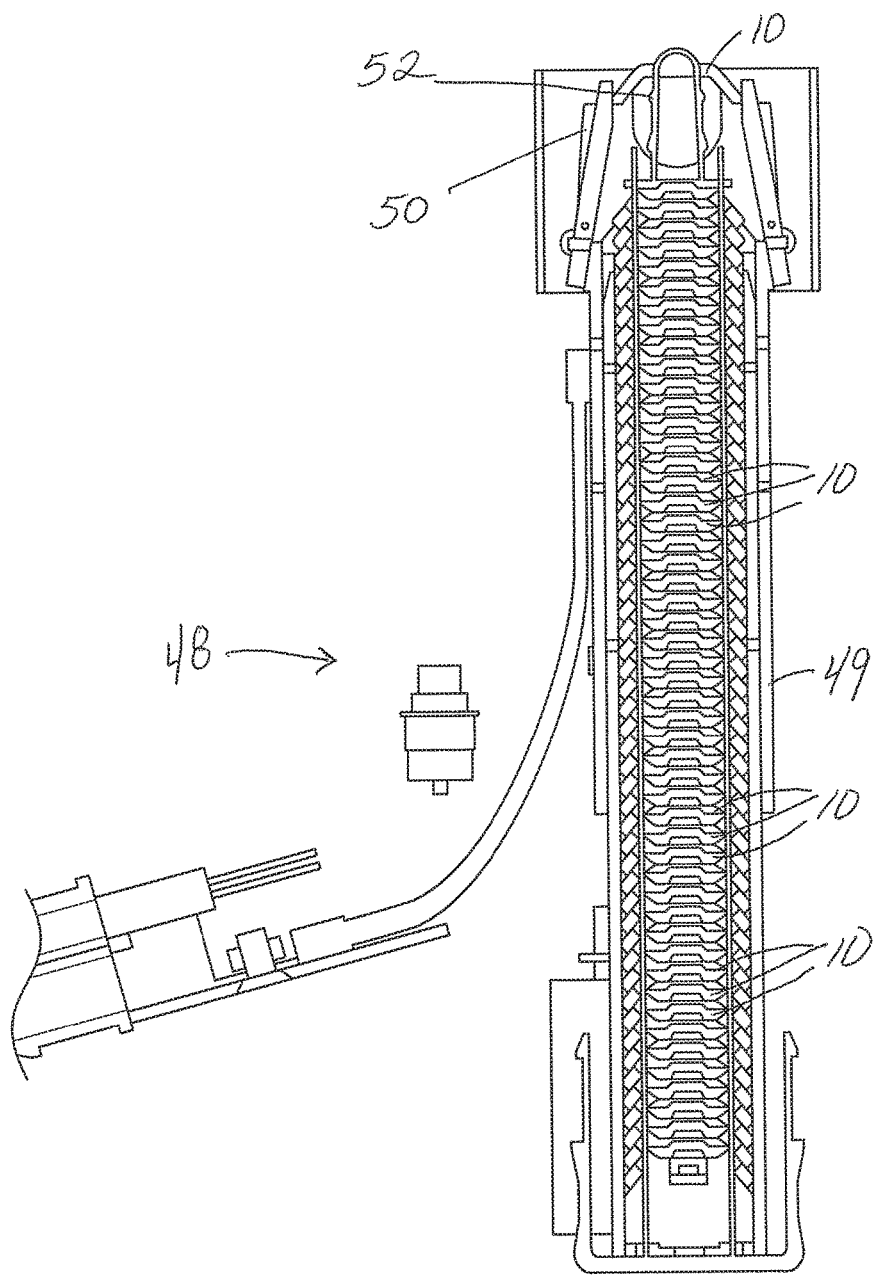
FIG. 10 is a partial cross-sectional view of a second weld tool having a magazine holding a plurality of stackable routing clips.

During use, the stackable routing clips 10 may be individually dispensed, deployed, or feed from the magazine 42 to the weld tool 44. For example, the magazine 42 or the weld tool 44 may include a button or lever that deploys a routing clip 10 from the stack of routing clips 10. The pressing of the button or lever may actuate or release an arm 46, which may be spring loaded. The arm 46 may be positioned and configured to engage a surface of one routing clip 10 in the stack of clips 10, such as, for example, the first or second side 22, 24 outer surface 26, upper face 16, and/or top surface 28 of the routing clip 10 that is being dispensed. Alternatively, rather than pressing a button or lever, the operator may engage the arm 46 so as to facilitate' the dispensing of the one clip 10. The arm 46 may then push the routing clip 10 through a dispensing pathway and/or outlet. For example, according to the embodiment illustrated in FIG. 8, the clip 10 being dispensed may be moved by the arm 46 generally in a direction that is perpendicular to the axis of the stack of routing clips 10 in the magazine 42 so as to be in proximity to a welding tip of the weld tool 44. In another application, such as the use of the second weld tool 48 illustrated in FIG. 10, a routing clip 10 may be dispensed from the stack of clips 10 in a magazine 49 in a direction that is generally parallel to the axis of the stack of clips 10.

However, according to other embodiments, the stackable routing clips 10 may be affixed to a target surface without using a dispenser.

Further, the magazine 42, 49 and/or weld tool 44, 48 may be configured to retain the dispensed routing clip 10 at a dispensed location relative to the weld tool 44 such that the dispensed routing clip 10 may be moved or positioned by the operator moving the weld tool 44. For example, as shown at least in FIG. 10, the weld tool 48 may include retaining arms or clips 50 that retain the position of the dispensed clip 10 in a position for engagement by the weld tool 44. Such a retained position may include generally aligning the groove 38 of the routing clip 10 with a welding tip 52 of the weld tool 48. FIG. 9 also illustrates a welding tip 47', 47" of the weld tool 44 and a dispensed clip 10', 10" at a first and second position. When in the first position, a clip 10' is dispensed from a dispenser, such as magazine 42, so that the dispensed routing clip 10' is adjacent to the welding tip 47' of the weld tool 44. According to certain embodiments, the operator may then move the weld tool 44 and the dispensed clip 10' from the first position to the second, or weld, position. With the clip 10" at the second position, the operator may activate the weld tool 44, 48, which causes an arc that melts at least a portion of the weld projection 36 of the routing clip 10" to form a pool of molten metal. Further, the weld tip 47" may be used, as well as other portions of the weld tool 44, to plunge the clip 10" into the molten metal formed by the melted weld projection 36, where the stackable routing clip 10" may be welded in place. The resultant weld may be between the weld projection 36 and at least a portion of lower face 18 and the target surface of the machinery. The operator may then pull the weld tool 44, 48 away from the welded routing clip 10".

There are a number of different ways cables may be secured to the stackable routing clip 10. For example, according to certain embodiments, the routing clip 10 may have only one wing section 20. Accordingly, a bundle of cables may be positioned adjacent to the wing section 20 and secured to the stackable routing clip 10 by a cable tie that is routed through the routing port 32 of the wing section 10. In embodiments having multiple wing sections 20, the cables may be positioned between at least two wing sections 20. Accordingly, a cable tie maybe routed through the routing port 32a of the first wing section 20a, over the cables, through the routing port 32b of the second wing section 20b, and fastened. Alternatively, for relatively small bundle of cables, the cables may be routed closer to a single wing section 20 such that the cable tie may be routed through the routing port 32 of only one wing section 20, even if the clip 10 has multiple wing sections 20. Further, a bundle of cables may be routed outside of the wing sections 20. In such situations, the cable tie may be routed around the cable bundle and through a routing port 32 of a single wing section 20. For larger bundles of cables, two stackable routing clips 10a, 10b may be used, where the clips 10a, 10b are welded to the machinery at a distance away from each other that is generally approximately equal to the width of the cable bundle. The cable bundle may then be routed between the clips 10a, 10b, and the cable tie may be routed through a routing port 32 of a first clip 10a, over the cables, and through a routing port 32b of a second clip 10b, and fastened to the first clip 10a.

The installation of the stackable routing clips 10 offers several advantages over the typical oval shaped and open-ended wire mounts. The installation of the stackable routing clip 10 involves a single weld versus two or more welds for such wire mounts. Additionally, the welding process used in installing the stackable routing clip 10 is relatively automated with use of the weld tool 44, 48 and dispenser, such as a magazine 42, 49, containing a stack of the stackable routing clips 10, which eliminates the need to use a skilled welder to install the routing clip 10. Compared to at least the traditional use and securement of hand-manipulated oval or open-ended wires, the use of a magazine 42, 49 may also reduce the time spent handling and positioning the clip 10.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A stackable routing clip that is to be secured to machinery by a weld tool comprising:
    a body having a first side, a second side, a first end, and a second end, the body having an upper face and a lower face that each extend between the first side and the second side, the body including a weld projection formed in the body that extends from the lower face of the body formed inside of the first side and the second side, the weld projection defining an indentation disposed along the upper face; and
    a first wing section and a second wing section each having a top surface, a bottom surface, and a routing port, the routing port comprising an inner surface that includes angled surfaces that assist with receiving an insertion of at least one cable tie, the first wing section extending from the first end of the body toward the upper face to form an obtuse angle at the top surface of the first wing section and the upper face at the first end of the body, and the second wing section extending from the second end of the body toward the upper face to form the obtuse angle at the top surface of the second wing section and the upper face at the second end of the body.

2. The stackable routing clip of claim 1, wherein the obtuse angle is approximately a 127 degree angle.

3. The stackable routing clip of claim 1, wherein:
    a first extension extends from the first side of the body to join the first side to a first portion of an outer side of one of the first wing section or the second wing section,
    a second extension extends from the second side of the body to join the second side to a second portion of the outer side of the one of the first wing section or the second wing section,
    a distance between where the first and second extensions extend from first and second sides being equal to a first body width,
    a distance between where the first and second extensions meet the first and second portions of the outer side being equal to a first wing width, and
    the first wing width being larger than the first body width.

4. The stackable routing clip of claim 1, wherein the weld projection includes a flux that is configured to facilitate securing the stackable routing clip to the machinery by the weld tool.

5. A plurality of the stackable routing clip of claim 1, wherein the plurality of the stackable routing clip comprises a first stackable routing clip and a second stackable routing clip, and wherein the body, the first wing section, and the second wing section of the first stackable routing clip are stacked against the second stackable routing clip in a dispenser for the weld tool.

6. A stackable routing clip that is to be welded to machinery by a weld tool and which is useable with a cable tie fastener to secure a cable to machinery, the stackable routing clip comprising:
    a body having an upper face and a lower face, the body including a weld projection that extends from the lower face of the body; and
    a first wing section and a second wing section each having a top surface, a bottom surface, and a routing port, the routing port configured to receive an insertion of the cable tie fastener, the routing port having an enclosed outer perimeter, the enclosed outer perimeter configured to provide a surface between an outer side of each of the first wing section and the second wing section and the routing port to secure the cable tie fastener to one or both of the first wing section and the second wing section; and
    wherein a first extension, between the upper face and the lower face of the body, extends from a first side of the body to join the first side to a first portion of the outer side of one of the first wing section or the second wing section, and a second extension, between the upper face and the lower face of the body, extends from a second side of the body to join the second side to a second portion of the outer side of the one of the first wing section or the second wing section, a distance between where the first and second extensions extend from first and second sides being equal to a first body width, a distance between where the first and second extensions meet the first and second portions of the outer side being equal to a first wing width, the first wing width being larger than the first body width.

7. The stackable routing clip of claim 6, wherein the first wing section extends from a first end of the body to form an obtuse angle at the top surface of the first wing section and the upper face at the first end of the body, and the second wing section extends from a second end of the body to form the obtuse angle at the top surface of the second wing section and the upper face at the second end of the body.

8. A plurality of the stackable routing clip of claim 7, wherein the plurality of the stackable routing clip comprises a first stackable routing clip and a second stackable routing clip, and wherein the body, the first wing section, and the second wing section of the first stackable routing clip are stacked against the second stackable routing clip in a dispenser for the weld tool.

9. The stackable routing clip of claim 7, wherein the stackable routing clip is configured such that, when n stackable routing clips are stacked together, a stacked length of the n stackable routing clips is less than a sum of individual lengths of each of the n stackable routing clips, and wherein n is an integer greater than 1.

10. A plurality of the stackable routing clip of claim 7, wherein the plurality of the stackable routing clip comprises a first stackable routing clip and a second stackable routing clip, and wherein the first and the second stackable routing clips are stacked so that at least a portion of the bottom surface of the first wing section and the second wing section of the first stackable routing clip rests upon at least a portion of the top surface of the first wing section and the second wing section of the second stackable routing clip.

11. The stackable routing clip of claim 6, wherein the first wing section and the second wing section are configured to allow the cable tie fastener to be fastened to both of the first wing section and the second wing section and extend above the upper face of the body.

12. The stackable routing clip of claim 11, wherein an inner surface of the routing port includes a ramp that is configured to assist in facilitating with routing of the cable tie fastener through the routing port after the stackable routing clip is welded to the machinery.

13. The stackable routing clip of claim 6, wherein the weld projection defines an indentation disposed along the upper face of the body.

14. The stackable routing clip of claim 13, wherein the weld projection includes a flux material that is configured to facilitate securing the stackable routing clip to the machinery by the weld tool.

* * * * *